United States Patent [19]

English et al.

[11] Patent Number: 5,837,352
[45] Date of Patent: Nov. 17, 1998

[54] MECHANICALLY COMPATIBILIZED FILM/ NONWOVEN LAMINATE

[75] Inventors: Karen Lynn English, Marietta; Ann Louise McCormack, Cumming, both of Ga.

[73] Assignee: Kimberly-Clark Worldwide, Inc., Neenah, Wis.

[21] Appl. No.: 874,057

[22] Filed: Jun. 12, 1997

Related U.S. Application Data

[63] Continuation of Ser. No. 359,985, Dec. 20, 1994, abandoned.

[51] Int. Cl.⁶ .................................................. B32B 27/14
[52] U.S. Cl. ..................... 428/198; 428/373; 428/374; 428/903; 442/395; 442/396; 442/397; 442/398; 442/400; 442/401; 442/409; 128/849; 604/358; 604/365; 604/366; 604/367
[58] Field of Search ................................ 428/198, 373, 428/374, 903; 442/395, 396, 397, 398, 400, 401, 409, 849; 128/849; 604/358, 365, 366, 367

[56] References Cited

U.S. PATENT DOCUMENTS

| | | |
|---|---|---|
| 3,276,944 | 10/1966 | Levy . |
| 3,338,992 | 8/1967 | Kinney . |
| 3,341,394 | 9/1967 | Kinney . |
| 3,502,538 | 3/1970 | Petersen . |
| 3,502,763 | 3/1970 | Hartmann . |
| 3,542,615 | 11/1970 | Dobo et al. . |
| 3,676,242 | 7/1972 | Prentice . |
| 3,692,618 | 9/1972 | Dorschner et al. . |
| 3,802,817 | 4/1974 | Matsuki et al. . |
| 3,849,241 | 11/1974 | Butin et al. . |
| 3,973,063 | 8/1976 | Clayton . |
| 4,041,203 | 8/1977 | Brock et al. . |
| 4,087,486 | 5/1978 | Fielding et al. . |
| 4,104,404 | 8/1978 | Bieler et al. . |
| 4,185,135 | 1/1980 | Huff . |
| 4,254,175 | 3/1981 | Kubat et al. . |
| 4,340,563 | 7/1982 | Appel et al. . |
| 4,522,203 | 6/1985 | Mays . |
| 4,595,629 | 6/1986 | Mays . |
| 4,606,970 | 8/1986 | Sharps, Jr. . |
| 4,741,944 | 5/1988 | Jackson et al. .......................... 428/152 |
| 4,761,324 | 8/1988 | Rautenberg et al. . |
| 4,929,303 | 5/1990 | Sheth . |
| 4,935,287 | 6/1990 | Johnson et al. . |
| 4,983,450 | 1/1991 | Yanagihara et al. . |
| 5,011,698 | 4/1991 | Antoon, Jr. et al. . |
| 5,116,662 | 5/1992 | Morman . |
| 5,143,679 | 9/1992 | Weber et al. . |
| 5,169,712 | 12/1992 | Tapp ..................................... 428/315.5 |
| 5,208,098 | 5/1993 | Stover . |
| 5,261,899 | 11/1993 | Visscher et al. . |
| 5,336,552 | 8/1994 | Strack et al. . |

FOREIGN PATENT DOCUMENTS

| | | |
|---|---|---|
| 803714 | 1/1969 | Canada . |
| 0 505 027 A1 | 9/1992 | European Pat. Off. . |
| 3724510 A1 | 2/1989 | Germany . |
| 6-1072543 | 4/1986 | Japan . |
| 4-227260 | 8/1992 | Japan . |
| 2155853 | 10/1985 | United Kingdom .............. B32B 5/18 |
| 2 285 408 | 7/1995 | United Kingdom . |
| 2 290 052 | 12/1995 | United Kingdom . |
| WO 93/21013 | 10/1993 | WIPO . |

OTHER PUBLICATIONS

NRL Report 4364, "Manufacture of Superfine Organic Fibers" by V.A. Went et al., May 1954.

NRL Report 5265, "An Improved Device for the Formation of Superfine, Thermoplastic Fibers" by K.D. Lawrence et al., Feb. 1959.

*Primary Examiner*—Helen L. Pezzuto
*Attorney, Agent, or Firm*—Nicholas N. Leach; Patrick C. Wilson; James B. Robinson

[57] ABSTRACT

Disclosed herein is a film/nonwoven laminate which incorporates a low gauge machine direction oriented film layer laminated to a nonwoven support layer. The individual layers are designed such that the film layer in the laminated state has an elongation at break value in the cross machine direction that is greater the elongation at peak load value for the nonwoven layer in the same direction. Consequently, if the laminate is subjected to severe stretching forces in the cross machine direction, the nonwoven layer will fail before the film layer. In addition, the laminate has a peak load value of at least 300 grams. As a result, the laminate is particularly useful as, for example, an outercover material for personal care absorbent articles.

9 Claims, 2 Drawing Sheets

MECHANICALLY COMPATIBILIZED FILM/NONWOVEN LAMINATE

This application is a continuation of application Ser. No. 08/359,985 entitled "Mechanically Compatibilized Film/Nonwoven Laminate" and filed in the U.S. Patent and Trademark Office on Dec. 20, 1994 now abandoned. The entirety of this application is hereby incorporated by reference.

FIELD OF THE INVENTION

The present invention is directed to machine direction oriented films and their use in film/nonwoven laminates. More particularly the present invention is directed to film/nonwoven laminates having very low gauge films and improved cross machine direction integrity in the laminate.

BACKGROUND OF THE INVENTION

Film/nonwoven laminates are used in a wide variety of applications not the least of which is as outercovers for personal care absorbent articles such as diapers, training pants, incontinence garments, feminine hygiene products, wound dressings, bandages and the like. Film/nonwoven laminates also have applications in the health care area in conjunction with such products as surgical drapes and gowns and other apparel for clean room, health care and other related uses. In the personal care area in particular, there has been an emphasis on the development of low cost laminates which have good barrier properties, especially with respect to liquids, as well as good aesthetic and tactile properties such as hand and feel. To this end, it has become increasingly more advantageous to use films which are thinner and thinner. Thinner films are lower in cost and, because of their reduced gauge, oftentimes softer and more quiet. Thinner films also can be made more breathable.

Thinner films, which sometimes have an effective gauge or thickness less than 25 micrometers (microns), also tend to be fairly weak. This is especially true in the cross machine direction since to obtain such low thicknesses the films are often highly stretched in the machine direction. Severe orientation in the machine direction tends to orient the polymer molecules making up the film. Such orientation can greatly increase the strength of the film in the machine direction but it also tends to weaken the same film in the cross machine direction. By laminating a support layer such as a fibrous nonwoven web to the film layer, a laminate can be created with additional properties. The nonwoven layer can add increased strength to the overall composite. In addition, it can impart such properties as a cloth-like feel which is important in many applications including personal care absorbent articles. Unfortunately, heretofore film/nonwoven laminates have not always provided optimum benefits especially in the area of strength. As a result, the film portions of such laminates have tended to fail thereby providing less than optimum performance in the overall product. This has been especially true when the film of the film/nonwoven laminate has been utilized as a barrier material as, for example, an outercover for a personal care absorbent article. Consequently, there is a need for improved film/nonwoven laminates, especially in cases where the film layer has been highly oriented in a single direction and the overall thickness of the film has been greatly reduced.

SUMMARY OF THE INVENTION

Figure 1:
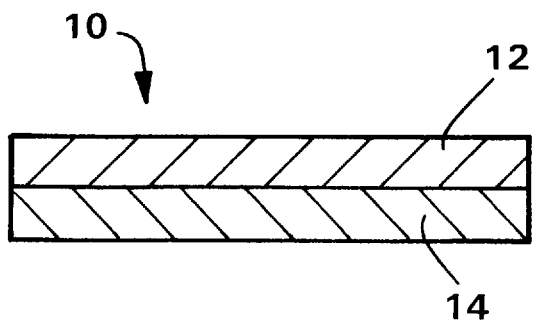
FIG. 1 is a cross-sectional side view of a film/nonwoven laminate according to the present invention.

The present invention is directed to mechanically compatibilized film and nonwoven laminates wherein the film layer has been oriented in the machine direction before it has been attached to a support layer such as a fibrous nonwoven web.

Many products today especially in the area of disposable products such as personal care absorbent products, utilize films and fibrous nonwoven webs as components. From a cost standpoint, it is often desirable to make the materials as low gauge as possible. One way to do this with films is to orient the film, for example, in the machine direction to lower the gauge or thickness of the film. In orienting the film, the film will generally pick up strength in the machine direction (the direction of stretching) but at the same time will lose strength in the cross machine direction (the direction perpendicular to the direction of stretching). As a result, a support layer such as a fibrous nonwoven web is laminated to the film layer to add strength.

The film layer, support layer and laminate all have a machine direction and a cross machine direction. Prior to lamination, the film layer is oriented in the machine direction so that is has an effective gauge or thickness of about 13 micrometers (microns) or less. The fact that the film layer has been oriented in the machine direction can be determined by comparing the machine and cross machine direction strengths of the oriented film. An oriented film will have a strength in one direction as measured by the strip tensile test described below which is at least twice the strength in the direction generally perpendicular to the first direction. The direction with the stronger strength will be the machine direction and the direction with the weaker strength will be the cross machine direction. The film layer, the fibrous nonwoven support layer and the laminate all have or define a machine direction and a cross machine direction with the machine directions of the film and nonwoven layers having been aligned with one another in the machine direction prior to lamination.

The film layer after machine direction orientation and lamination defines a film elongation at break value which is measured in the cross machine direction. Due to the fact that it is hard to delaminate the sample materials, as described below, a separate piece of the film material is oriented and then sent through the bonding equipment with a release paper in order to obtain a nipped film which can be used to measure the film elongation at break value for a film which has been oriented and laminated. This value is then compared to the elongation at peak load value in the cross machine direction for the fibrous nonwoven layer and the film elongation at break value in the cross machine direction must be greater than the elongation at peak load value for the nonwoven.

The film layer, fibrous nonwoven web support layer and the laminate all define individual peak load values. In the cross machine direction, the nonwoven peak load value is greater than the film peak load in the cross machine direction. In addition, the film peak load is less than the laminate peak load in the cross machine direction with the laminate peak load in the cross machine direction being at least 300 grams.

The support layer can be made from a wide variety of materials including various fibrous nonwoven webs. Examples of such webs include, but are not limited to, spunbond nonwoven webs an laminates such as spunbond/meltblown and spunbond/meltblown/spunbond webs. With spunbond/meltblown webs it is generally more desirable to attach the meltblown portion of the laminate to the film layer. In addition, in certain applications it may be desirable to add additional layers to the film/nonwoven laminate such as, for example, a second nonwoven or other support layer to the surface of the film layer which is opposite that of the other nonwoven layer. Here again, the second support layer may be, for example, as single layer of nonwoven material or a laminate such as a spunbond/meltblown/spunbond laminate.

The film/nonwoven laminate of the present invention has a wide variety of applications including uses in personal care absorbent articles such as diapers, training pants, incontinence garments, sanitary napkins, wound dressings, bandages and the like. Typically such article will have a liquid pervious top sheet and a back sheet with an absorbent core disposed between the top sheet and the back sheet. If the film layer of the film/nonwoven laminate is made to be liquid pervious, it can be used as the top sheet. If it is substantially liquid impervious, it can be used as the back sheet. Other applications would include, but not be limited to, using the film/nonwoven laminate according to the present invention as all or a portion of such products as surgical drapes and gowns as well as well as article of clothing in general. In many of these applications it may be desirable for the laminate to be breathable in which case the laminate should have a water vapor transmission rate of at least 300 grams per square meter.

DETAILED DESCRIPTION OF THE INVENTION

The present invention is directed to a film/nonwoven laminate with increased cross machine direction (CD) integrity as a result of its improved design and the matching of properties in both the film layer and the nonwoven layer. The film employed in the present invention has been oriented in the machine direction (MD) generally a sufficient amount to yield a film with an effective gauge or thickness less than 13 microns. Such orientation will often require that the film be stretched at least two times their original or unstretched length. Once the film has been oriented, it is then laminated to a fibrous nonwoven web using heat and pressure such as with heated calender rolls or by ultrasonic bonding techniques. Alternatively, the two layers can be laminated together using adhesives.

Critical to the design of a film/nonwoven laminate according to the present invention are the stress(load) versus strain(elongation) properties of each of the film, the nonwoven and the laminate including the elongation-to-break and peak load at break properties of the same three materials. Heretofore, film/nonwoven laminates using MD oriented films have sometimes failed because the film portions of the laminates have torn or ruptured prematurely. The present invention takes into account the properties of each of the components and other necessary design parameters including film thickness, MD orientation of the film and certain minimum strain requirements for the film to yield an improved film/nonwoven laminate.

Referring to FIG. 1, the film/nonwoven laminate 10 according to the present invention includes a film layer 12 and a support layer 14 which can be made from a number of materials including, for example, films, nonwovens, scrims, wovens and combinations of the foregoing provide the support layer 14 and the overall laminate 10 have the properties specified herein. Fibrous nonwoven webs have been found to work particularly well from the standpoint of economics, aesthetic properties and strength. Polymer selection for the support layer 14 is not critical provided proper adhesion and strength properties can be achieved. Suitable polymers would include but would not be limited to polyolefins and other thermoplastic polymers. Suitable fibrous nonwoven web forming processes would include, for example, spunbonding and meltblowing processes. Meltblown fibers are formed by extruding molten thermoplastic material through a plurality of fine, usually circular, die capillaries as molten threads or filaments into a high velocity usually heated gas stream such as air which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described in various patents and publications including NRL Report 4364, "Manufacture of Super-Fine Organic Fibers" by B. A. Wendt, E. L. Boone and C. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676, 242, issued Jul. 11, 1972, to Prentice; and U.S. Pat. No. 3,849,241, issued Nov. 19, 1974, to Buntin, et al. The foregoing references are incorporated herein by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbond nonwoven webs is illustrated in patents such as Appel et al., U.S. Pat. No. 4,340,563; Matsuki, et al, U.S. Pat. No. 3,802,817; Dorschner et al., U.S. Pat. No. 3,692, 618; Kinney, U.S. Pat. No. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent Number 803,714. All of the foregoing references are incorporated herein by reference in their entirety.

Fibrous nonwoven webs made from multiconstituent and multicomponent fibers such as, for example, bicomponent fibers can also be used to form the support layer 14. See for example, U.S. Pat. No. 5,336,552 to Strack et al. which describes how to make bicomponent spunbond nonwoven webs. The Strack et al. patent is incorporated herein by reference in its entirety.

It is also possible to form laminates for use as the support layer 14 such as spunbond/meltblown laminates and spunbond/ meltblown/spunbond laminates as are taught, for example, in U.S. Pat. No. 4,041,203 to Brock et al. which is incorporated herein by reference in its entirety.

The film layer 12 may be a single or mono layer film or a multi-layer film such as is formed using a coextrusion process. The formation of films is well know to those of ordinary skill in the film forming art and need not be discussed herein in detail. There are a large number of vendors who can manufacture such films to exacting specifications. Suitable film forming polymers include, but are not limited to, homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU) and olefinic thermoplastic elastomers which are multistep reactor products wherein an amorphous ethylene propylene random copolymer is molecularly dispersed in a predominately semicrystalline high polypropylene monomer/low ethylene monomer continuous matrix. If desired, it is also possible to add fillers to the film layer 12 such as, for example, calcium carbonate and titanium dioxide to increase opacity, decrease cost and/or create a breathable film if the filled film is subsequently stretched or crushed.

If the film layer 12 is not sufficiently thin, typically less than 13 microns, then it may be necessary to further thin the film by stretching it in an apparatus like a machine direction orienter (MDO) unit such as is commercially available from the Marshall and Williams Company of Providence, R. I. An MDO unit has a plurality of stretching rollers which progressively stretch and thin the film in the machine direction which is the direction of travel of the film through the apparatus.

Once the film has been formed and optionally thinned to where it has an effective thickness less than 13 microns, it is then laminated to the support layer 14. Suitable lamination means include, but are not limited to, adhesives, ultrasonic bonding and thermomechanical bonding as through the use of heated calendering rolls. Such calendering rolls will often include a patterned roll and a smooth anvil roll, though both rolls may be patterned or smooth and one, both or none of the rolls may be heated.

The problem that was occurring with previous film/nonwoven laminates as identified by the present applicants was that the film portion of the laminates was tearing when the laminate was being used as an outercover for diapers. As a result, the stress and strain properties for each of the materials were studied. Strain is related to the amount of elongation that a material can withstand before breaking. Based upon this study, it was determined that the degree of strain or elongation at break for the film in the cross-machine direction had to be greater than the elongation at peak load value for the nonwoven layer or the overall laminate in the cross-machine direction. The stress or load on the film was also determined to have to be less than that of the nonwoven and the laminate in the cross-machine direction. In addition, it was determined that in order for the overall laminate to perform well, the laminate had to be able to withstand a certain minimum load without failing, namely, at least 300 grams using the one inch cut strip tensile test described below.

In view of the foregoing, laminates were prepared wherein the film had either less, approximately equal or a greater elongation at break than the elongation at peak load for the nonwoven. Stress/strain data were prepared for these various films (machine direction oriented), nonwovens and laminates. In all cases, the film had an inherently lower peak load or strength than that of the nonwoven or the laminate in the cross machine direction. The elongation of the nonwoven and laminate was measured at the peak load as opposed to at failure for the nonwoven and laminate. The elongation at break for the film was greater than the elongation at peak load for the nonwoven and laminate. However, in visually observing the sample laminates as they were stretched, it was observed that the films were still failing prematurely. By prematurely it is meant that the films were tearing in the cross machine direction and/or holes were forming before and as the nonwoven began to tear.

Additional testing was then performed on a post-bonded or "nipped film" with the hypothesis being that the film was further weakened in the cross machine direction due to the lamination process.

Separating the laminate to obtain samples of the film for testing was difficult. As a result, a method was devised to nip the film independently of the nonwoven. To do this, samples of the film were run through the same bonding process but without the nonwoven. Instead, the film was run through the bonding equipment in conjunction with a silicone coated release paper having a basis weight of 125 gsm. The samples were run through the same patterned bonding roll and a smooth anvil rolls as were used to make the laminate materials. The patterned roll had a bond area of approximately 15 to 24 percent per unit area of the roll. The two films were run through the bonder such that the film used in the laminate was adjacent the anvil roll and the release paper was adjacent the patterned roll. The line speed for the bonding process was 61 meters per minute. The bonding pressure along the line of contact between the two bonding rolls was 4,218 kilograms per meter (kg/m). Once the bonding process had been completed, the film was allowed to cool and it was then manually peeled away from the silicone release paper and was subsequently subjected to stress/strain analysis for properties in the cross machine direction.

As was confirmed by the testing, the lamination process was weakening the film in the cross machine direction. Film failure in the laminate was occurring at similar elongations to the observed elongation at break of the nipped film. As a result, it was determined that the film and laminate would have better resistance to tearing and failure if the elongation at break in the cross machine direction of the nipped film was at least 10 percent greater that the elongation at peak load value in the nonwoven to compensate for the reduction in this property in the nipped film due to the lamination process.

In view of the foregoing, a series of samples were prepared and tested in accordance with the above theory. The examples and testing procedures are set forth below.
TEST PROCEDURES The following test procedures were used to help analyze the examples set forth below. The test procedures for elongation and strain included elongation at break and at peak load as well as load at break and peak load. Other testing included film thickness or effective gauge. All values were measured in the cross-machine direction for the films, nonwovens and laminates. In addition, when the laminates were made, the film layer and the nonwoven layers were aligned prior to lamination such that the machine direction orientation of each layer was parallel to one another.
Effective Gauge The effective gauge of a material was calculated by dividing the basis weight of the film layer by the density of the polymer(s) and fillers forming the film.

The effective gauge of a layer of film was calculated by multiplying 0.001334 (a metric to English conversion factor) times the weight per unit area of the film sample in ounces per square yard and dividing the result by the density of the polymer formulation in grams per cubic centimeter to yield the effective gauge in inches.
One Inch Cut Strip Tensile Test The film and nipped film peak load and elongation at break as well as nonwoven and laminate peak load and elongation at peak load were determined in accordance with Method 5102 Federal Test Methods Standard Number 191A. Sample sizes were one inch by six inches (2.54 cm×15.24 cm) with the cross machine direction of the sample running parallel to the six inch length of the sample. Three samples were run for each material and the values were averaged. The jaws of the tensile tester were one inch wide, the initial gap or gauge length was three inches (7.62 cm) and the crosshead speed was 12 inches per minute (305 mm/min).

Grab Tensile

The grab tensile properties of the laminate were determined in accordance with Method 5102 Federal Test Methods Standard Number 191A. Sample sizes were four inches by six inches (10.16 cm×15.24 cm) with the cross machine direction of the sample running parallel to the six inch length of the sample. Ten samples were run for each material. The jaws of the tensile tester were three inches wide, the initial gap or gauge length was three inches (7.62 cm) and the crosshead speed was 100 millimeters per minute.

During the test, the failure mode of the samples was observed. For materials according to the present invention, in addition to having to have the elongation and load properties defined herein, in eighty percent of the samples (sample base of ten) there were no tears in the film prior to laminate or nonwoven failure. By failure it is meant that the nonwoven began to have tears before the film layer exhibited tears or pinholes itself. In addition, such failures took place above a 300 gram load.

EXAMPLES

A series of examples were created to demonstrate and distinguish the attributes of the present invention.

Example 1

In Example 1 a film/nonwoven laminate was created. The film layer contained, on a total weight percent basis based upon the weight of the film, 65 percent China Supercoat™ calcium carbonate with a 1 micron average particle size and a 7 micron top cut. The calcium carbonate was obtained from ECCA Calcium Products, Inc. of Sylacauga, Ala. The calcium carbonate was blended with 20 weight percent linear low density polyethylene made from a blend of Dowlex® 2517 linear low density polyethylene and Dowlex® 2532 linear low density polyethylene blended in a weight ratio of 1:4 such that the melt index of the blend was 10 M.I. (10 minutes at 190 degrees F.). The Dowlex® polymers are available from Dow Chemical U.S.A. of Midland, Mich. The remaining 15 percent of the formulation comprised Himont KS051P polypropylene-based polymer from Himont, USA of Wilmington, Del. The KS051P polymer is an olefinic thermoplastic elastomer or TPO multistep reactor product wherein an amorphous ethylene propylene random copolymer is molecularly dispersed in a predominately semicrystalline high propylene monomer/low ethylene monomer continuous matrix.

The film had an initial gauge of 38.1 microns and was stretched 3.75 times it original length to a thinned effective gauge of 10.7 microns using a machine direction orienter (MDO) model number 7200 from the Marshall and Williams Company of Providence, R.I. By saying that the film was stretched 3.75 times it is meant that a film which, for example, had an initial length of 1 meter if stretched 3.75 times would have a final length of 3.75 meters. The film was heated to a temperature of 77° C. and the film was run through the MDO at a line speed of 61 meters per minute to stretch the film. The film was then annealed at a temperature of 102° C. It had a final basis weight of 20 grams per square meter (gsm).

The fibrous nonwoven web was a 17 gsm spunbond web made from approximately 2.0 to 2.5 denier polypropylene fibers. The polymer used to make the spunbond web was Exxon 3445 polypropylene from the Exxon Chemical Company of Houston, Tex. The web was prebonded using discrete bond points with a total bond area of approximately 17 percent per unit area of web. Suitable bond patterns include those for example described in the Brock et al. patent referenced above.

Figure 2:
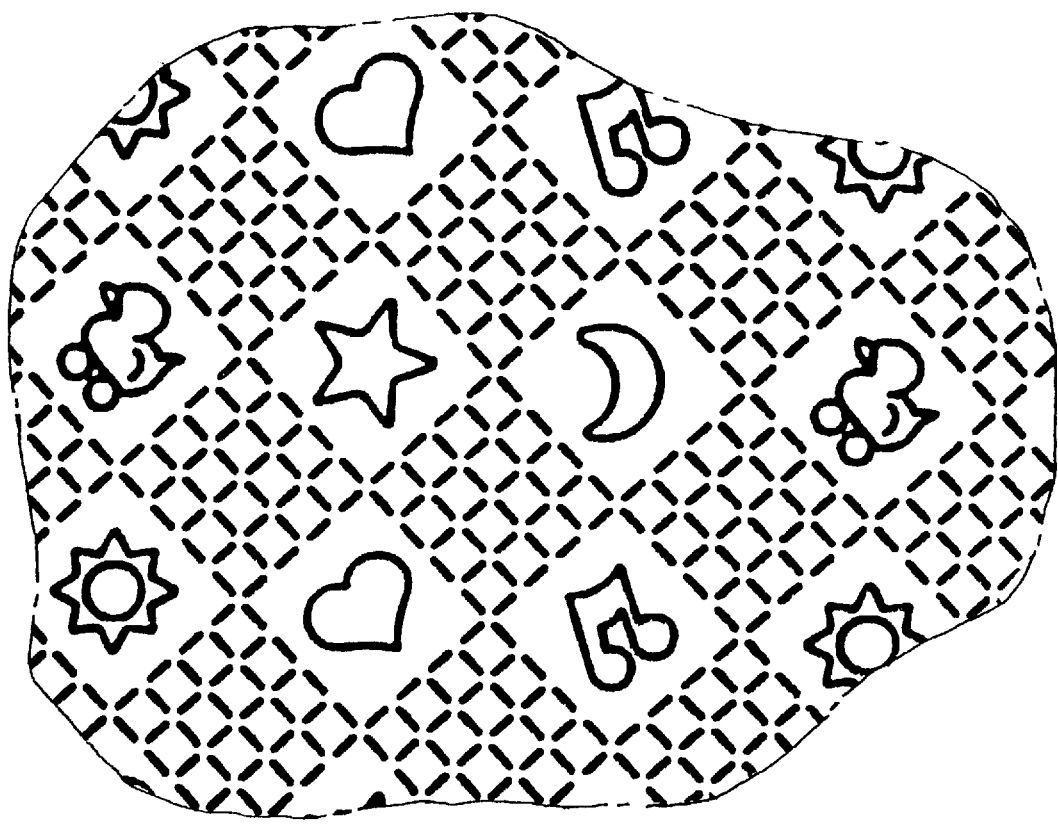
FIG. 2 is a top plan view to approximate scale of a baby objects bond pattern used to bond the film and support layers together for the examples.

Lamination of the two layers was effected using a patterned laminating roll with the baby objects bond pattern shown in FIG. 2 at a temperature of 74° C. and a smooth anvil roll at a temperature of 52° C. The film was positioned against the anvil roll and the pressure was set at 4,218 kilograms per meter (kg/m). The resultant laminate had a total bond area of 14 percent per unit area and a combined basis weight of 36.7 gsm.

Testing of the film (before and after being nipped), the nonwoven web and the laminate yielded the following properties (all values were measured for the cross machine direction):

Film CD peak load: 129.3 grams (g)
Film CD elongation at break: 111.5%
Nipped Film CD peak load: 79 g
Nipped Film CD elongation at break: 28%
Nonwoven CD peak load: 890.4 g
Nonwoven CD elongation at peak load: 35.4%
Laminate CD peak load: 1008.4 g
Laminate CD elongation at peak load: 43.9%

When the laminate was tested in the cross machine direction using the grab tensile test, the film was observed failing or tearing prior to the laminate failing. This demonstrated that if the nipped film elongation at break (28%) was less than the nonwoven elongation at peak load (35.4%), then the film would tear prematurely thus compromising the integrity and desireable barrier properties of the film/nonwoven laminate.

Example 2

In Example 2 another film/nonwoven laminate was created. The film layer was the same as that used in Example 1. The fibrous nonwoven web was a 29.1 gsm polypropylene spunbond web/meltblown web/ spunbond web laminate such as is described in the Brock et al. patent referenced above. The web was prebonded using discrete bond points with a total bond area of approximately 15 to 17 percent per unit area of web.

Lamination of the two layers was performed in the same manner and under the same conditions as in Example 1. The laminate had a basis weight of approximately 49.1 gsm.

Testing of the film (before and after being nipped), the nonwoven web and the laminate yielded the following properties (all values were measured for the cross machine direction):

Film CD peak load: 129.3 grams (g)
Film CD elongation at break: 111.5%
Nipped Film CD peak load: 79 g
Nipped Film CD elongation at break: 28%
Nonwoven CD peak load: 2196.7 g
Nonwoven CD elongation at peak load: 30.7%
Laminate CD peak load: 5720.7 g
Laminate CD elongation at peak load; 39.4%

When the laminate was tested in the cross machine direction using the grab tensile test, the film was observed, in this case, to fail or tear when the laminate failed. This demonstrated that if the nipped film elongation at break (28%) was similar in value to the nonwoven elongation at peak load(30.7%), the film and the nonwoven would fail at approximately the same time. This example demonstrated minimal performance of the film, however, it would be more desirable to be fail-safe and design the film elongation at break for the nipped film to be at least 10 percent greater than the nonwoven elongation at peak load in the cross machine direction to ensure barrier performance in use.

Example 3

In Example 3 a film/nonwoven laminate was created. The film layer was the same as that used in Example 1. The fibrous nonwoven web was a 13.4 gsm spunbond web made from 50/50 weight percent polypropylene/linear low density polyethylene uncrimped side-by-side bicomponent fibers having a denier of approximately 2.0 to 2.5. The polymers used to make the spunbond web were Exxon 3445 polypropylene and Dow 6811A linear low density polyethylene. The web was prebonded using discrete bond points with a total bond area of 15 to 17 percent per unit area of web.

Lamination of the two layers was effected in the same manner and under the same condition as in Example 1. The laminate had a basis weight of 33.4 gsm.

Testing of the film (before and after being nipped), the nonwoven web and the laminate yielded the following properties (all values were measured for the cross machine direction): Film CD peak load: 129.3 grams (g)

Film elongation at break: 111.5%

Nipped Film CD peak load: 79 g

Nipped Film CD elongation at break: 28%

Nonwoven CD peak load: 381.3 g

Nonwoven CD elongation at peak load: 65.2%

Laminate CD peak load: 415.6 g

Laminate CD elongation at peak load 71.1%

When the laminate was tested in the cross machine direction using the grab tensile test, the film was observed to fail or tear prior to laminate failure in a similar fashion to that of Example 1. This demonstrated that if the nipped film elongation at break (28%) was less than the nonwoven elongation at peak load (65.2%,) the film would again tear prematurely, thus destroying the integrity and desireable barrier properties of the film/nonwoven laminate.

Example 4

In Example 4 a film/nonwoven laminate was created. The film layer contained, on a total weight percent basis, based upon the weight of the film, 62 percent China Supercoat™ calcium carbonate with a 1 micron average particle size and a 7 micron top cut. The calcium carbonate was obtained from ECCA Calcium Products, Inc. of Sylacauga, Ala. The calcium carbonate was blended with 5 weight percent Dow 640I low density polyethylene and 13 percent Shell 6D81polyethylene/polypropylene random copolymer. The Dow polymer is available from Dow Chemical U.S.A. of Midland, Mich. and the Shell polymer is available from the Shell Chemical Company of Houston, Tex. The remaining 20 percent of the formulation comprised Himont KSO50 (flow modified to a 5 melt flow rate) polypropylene-based polymer from Himont, USA of Wilmington, Del. The KSO50 polymer is an olefinic thermoplastic elastomer or TPO multistep reactor product wherein an amorphous ethylene propylene random copolymer is molecularly dispersed in a predominately semicrystalline high propylene monomer/low ethylene monomer continuous matrix.

The film had an initial gauge of 38.1 microns and was stretched 4 times it original length to a thinned effective gauge of 10.7 microns using a machine direction orienter (MDO) model number 7200 from the Marshall and Williams Company of Providence, R.I. The film was heated to a temperature of 71° C. and the film was run through the MDO unit at a line speed of 61 meters per minute to stretch the film. The film was then annealed at a temperature of 85° C. It had a final basis weight of 20 gsm. The fibrous nonwoven web was the same as in Example 1.

Figure 3:
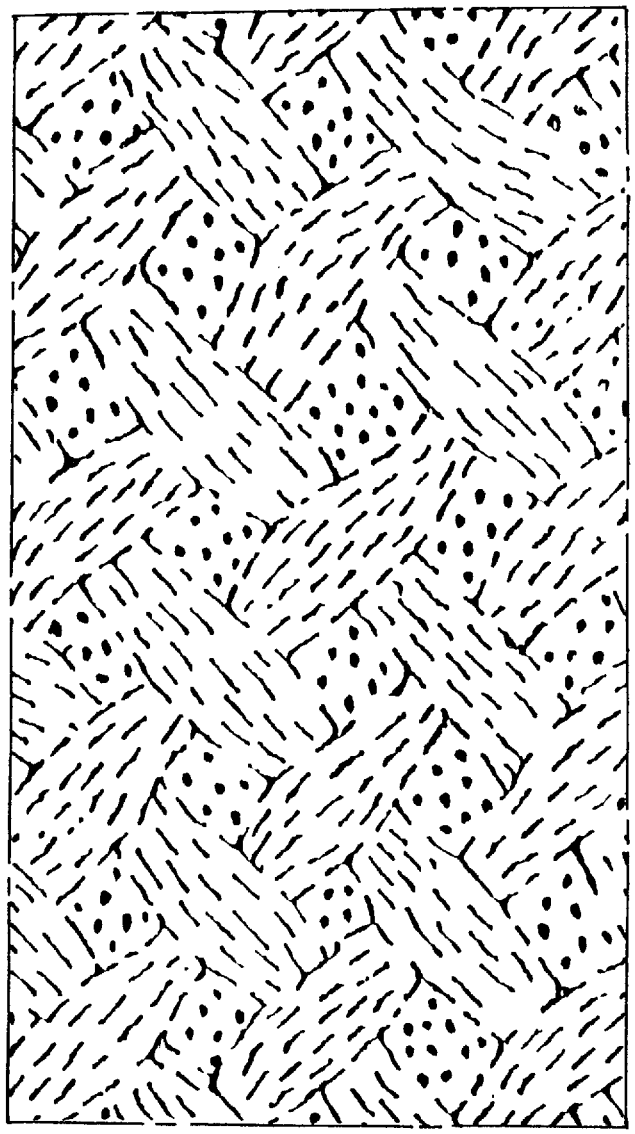
FIG. 3 is a top plan view to approximate scale of a woven web bond pattern used to bond the film and support layers together for the examples.

Lamination of the two layers was effected using a patterned laminating roll with a woven web bond pattern as shown in FIG. 3 at a temperature of 110° C. and a smooth anvil roll at a temperature of 66° C. The film was positioned against the anvil roll and the pressure was set at 4,570 kilograms per meter (kg/m). The resultant laminate had a total bond area of approximately 15 percent per unit area of the laminate and a combined basis weight of 36.7 gsm.

Testing of the film (before and after being nipped), the nonwoven web and the laminate yielded the following properties (all values were measured for the cross machine direction):

Film CD peak load: 160.2 grams (g)

Film CD elongation at break: 237.7%

Nipped Film CD peak load: 127.8 g

Nipped Film CD elongation at break: 266.9%

Nonwoven CD peak load: 890.4 g

Nonwoven CD elongation at peak load: 35.4%

Laminate CD peak load: 1194.3 g

Laminate CD elongation at peak load: 47.9%

When the laminate was tested in the cross machine direction using the grab tensile test, the film was observed not to fail or tear prior to laminate failure. In fact, the nonwoven clearly failed prior to film failure which is desireable. This demonstrated that if the nipped film elongation at break (266.9%) was greater than the nonwoven elongation at peak load (35.4%) the film would stay fully intact beyond the peak load of the laminate and only would fail as the nipped film elongation at break was reached. Thus the full integrity of the laminate was maintained well past the 300 gram load requirement.

Examples 1 and 3 demonstrated problematic film/nonwoven laminates that had the potential for premature film failure in use. Examples 2 and 4 demonstrated the invention as the film maintained integrity at or beyond laminate peak load.

Having thus described the invention in detail, it should be apparent that various modifications and changes can be made in the present invention without departing from the spirit and scope of the following claims.

We claim:

1. A film/nonwoven laminate comprising:

a film layer and a nonwoven layer laminated to one another to form a film/nonwoven laminate, said film layer having a machine direction and a cross machine direction, said nonwoven layer having a machine direction and a cross machine direction and said laminate having a machine direction and a cross machine direction, said film having been oriented in said machine direction prior to being laminated to said nonwoven layer, said film layer having an effective thickness of about 13 micrometers or less, said film layer after machine direction orientation and lamination defining a film elongation at break value in said cross machine direction, said nonwoven layer defining a nonwoven elongation at peak load value in said cross machine direction and said laminate defining an elongation at peak load value in said cross machine direction, said film elongation at break value in said cross machine direction being greater than said nonwoven elongation at peak load value in said cross machine direction, said film layer defining a film peak load value in said cross machine direction, said nonwoven layer defining a nonwoven peak load value in said cross machine direction, and said laminate defining a laminate peak load value in said cross machine direction, said nonwoven peak load value in said cross machine direction being greater than said film peak load value in said cross machine direction and said film peak load value in said cross machine direction being less than said laminate peak load value in said cross machine direction, said laminate peak load value in said cross machine direction being at least 300 grams.

2. The film/nonwoven laminate of claim 1 wherein said nonwoven layer comprises a spunbond nonwoven web.

3. The film/nonwoven laminate of claim 1 wherein said nonwoven layer comprises a spunbond nonwoven web and meltblown nonwoven web laminate.

4. The film/nonwoven laminate of claim 3 wherein said meltblown nonwoven web is attached to said film layer.

5. The film/nonwoven laminate of claim 1 wherein said nonwoven layer comprises a spunbond nonwoven web/meltblown nonwoven web/spunbond nonwoven web laminate.

6. The film/nonwoven laminate of claim 1 wherein said film elongation at break value in a laminated state in said cross machine direction is at least 10 percent greater than said nonwoven elongation at peak load value in said cross machine direction.

7. The film/nonwoven laminate of claim 1 which further includes a second nonwoven layer laminated to said film layer on a surface of said film layer opposite that of said nonwoven layer.

8. The film/nonwoven laminate of claim 7 wherein said nonwoven layer and said second nonwoven layer each comprise in order, a spunbond nonwoven web, a meltblown nonwoven web and a spunbond nonwoven web.

9. The film/nonwoven laminate of claim 1 wherein said laminate has a water vapor transmission rate of at least 300 grams per square meter per 24 hours.

* * * * *